United States Patent
Cecchi et al.

(10) Patent No.: US 6,623,956 B1
(45) Date of Patent: Sep. 23, 2003

(54) EMBRYO-CULTURING INCUBATOR ASSEMBLY

(75) Inventors: Michael D. Cecchi, Madison, CT (US); Jacques Cohen, New York, NY (US); Timothy Schimmel, Randolph, NJ (US); Monica Mezezi, Guelph (CA)

(73) Assignee: Genx International, INC, Guilford, CT (US)

( * ) Notice: Subject to any disclaimer, the term of this patent is extended or adjusted under 35 U.S.C. 154(b) by 179 days.

(21) Appl. No.: 09/693,595

(22) Filed: Oct. 20, 2000

(51) Int. Cl.[7] ............................................... C12M 1/00
(52) U.S. Cl. .................... 435/303.1; 435/809; 422/104; 422/99
(58) Field of Search .............................. 435/303.1, 809, 435/289.1; 422/99, 104; 312/351, 408, 32.2, 31.2, 209; 211/153, 134

(56) References Cited

U.S. PATENT DOCUMENTS

| | | | | |
|---|---|---|---|---|
| 335,097 A | * | 1/1886 | Swift | 239/44 |
| 2,643,931 A | * | 6/1953 | Anderson | 312/351 |
| 3,513,984 A | * | 5/1970 | Miller | 211/134 |
| 3,702,355 A | * | 11/1972 | Hayden | 264/264 |
| 4,570,744 A | * | 2/1986 | Hoshiba | 181/204 |
| 4,582,807 A | * | 4/1986 | Veeraraghavan | 435/32 |
| 5,601,143 A | * | 2/1997 | Binder | 165/61 |
| 5,792,427 A | * | 8/1998 | Hugh et al. | 219/407 |
| 6,450,349 B2 | * | 9/2002 | Lee | 211/85.18 |

\* cited by examiner

*Primary Examiner*—William H. Beisner
(74) *Attorney, Agent, or Firm*—William W. Jones

(57) ABSTRACT

An embryo culturing incubator is provided with a shelf configuration that enhances air circulation inside of the incubator, and enables unimpeded access to the individual embryo culture plates that are disposed on the shelves in the incubator. The incubator has an access door which allows one contact with the embryo culture plates on the incubator shelves. The shelves are configured so as to provide a useful free space between the inner surface of the incubator door and the frontal surface of the shelves in the incubator. The size of the free space allows a technician to reach all of the culture plates in the incubator without interfering with other culture plates in the incubator. The free space also allows for exemplary air circulation inside of the incubator.

5 Claims, 1 Drawing Sheet

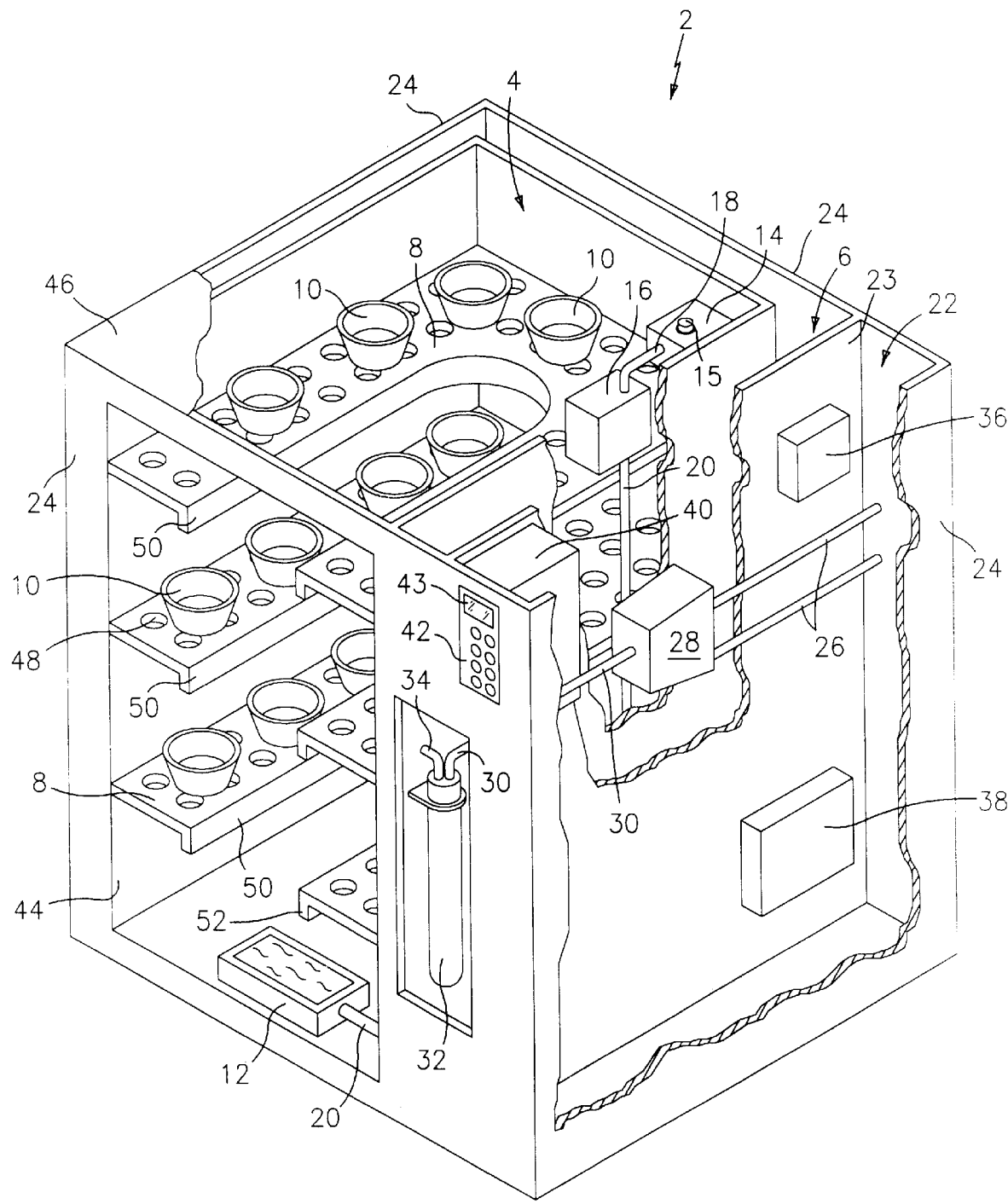

EMBRYO-CULTURING INCUBATOR ASSEMBLY

TECHNICAL FIELD

This invention relates to an apparatus for culturing or growing embryos in a communal environment. More specifically, this invention relates to an embryo culturing incubator assembly wherein individual embryo culturing plates in the incubator are disposed on shelves in the incubator. The shelves are configured relative to a door into the incubator so that air and other internal gases can freely circulate up and down through the incubator unimpeded by the shelves, and so that a technician can readily reach all of the culturing plates without being impeded by the incubator shelves.

BACKGROUND ART

Human, and other animal embryos, are presently grown in suitable growth-enhancing nutrients in specialized controlled atmosphere incubators. The growth period is typically about three days. After the growth period, the embryos are implanted into a female's reproductive system. There are several generally practiced embryo growth procedures which are presently in use. One of the generally practiced embryo growth techniques involves the use of a culturing container, such as a Petrie dish, in which individual embryos are placed in spaced-apart locations in the culturing dish. This technique involves the placement of individual embryos on a growth-enhancing nutrient in spaced apart positions in the Petrie dish, and subsequently immersing each of the individual embryos in a drop of a growth-enhancing nutrient.

Another of the generally practiced embryo growth techniques involves clustering a plurality of embryos together on a Petrie dish or in a growth tube, and covering the cluster with a common drop of the growth-enhancing nutrient. Using this technique, all of the embryos in a cluster are exposed to the same growth-enhancing nutrient drop and are able to share that growth-enhancing nutrient and also share their respective by-products of the growth process.

As noted above, the Petrie dishes or growth tubes are placed in an atmospherically controlled incubator. The incubators will typically include a plurality of shelves on which the Petrie dishes or growth tubes are placed. The shelves in a typical incubator assembly may be perforated so as to facilitate atmospheric or air circulation throughout the incubator. A typical embryo-culturing incubator assembly is shown and described in U.S. Pat. No. 5,792,427, granted Aug. 11, 1998 to Forma Scientific, Inc. The prior art incubators present certain problems relating to their ease of use, and to the ability of the individual embryos to be uniformly exposed to the growth-supporting atmosphere in the incubator. It would be highly desirable to provide an embryo-culturing incubator assembly which allows easy access to all of the embryo culturing plates in the incubator; and which also allows for free circulation of gases among all of the embryo culturing plates inside of the incubator.

DISCLOSURE OF THE INVENTION

This invention relates to an improved incubator assembly for growing embryos in vitro prior to implantation of the embryos in a female's reproductive system. The incubator assembly of this invention provides for easy access to all of the embryos being grown in the incubator, and also allows uniform distribution of the internal incubator atmosphere to all of the embryos being grown in the incubator. The embryos are disposed on individual growth dishes in the incubator. The incubator assembly includes a plurality of embryo growth dish trays which are vertically stacked above each other in the incubator, and on which the embryo growth dishes are disposed. The trays are provided with a frontal concavity which faces an access door to the incubator. The concavities allow a technician to reach into the side and rear recesses of each tray so as to be able to lift each of the embryo growth dishes off of each of the trays with disturbing any of the other embryo growth dishes.

The incubator assembly includes components such as an air-recirculating system, air filters, an air humidifying bubbler, and the like. The air in the incubator is recirculated through a particulate and volatile organic compound filter assembly by means of an air mover. The filter assembly is preferably capable of removing both particulates and volatile organic compounds from the recirculated gas stream. Air or other gases entering the incubator assembly for the first time are humidified by being passed through a bubbler. The recirculated and filtered atmosphere from inside of the incubator assembly is humidified by a liquid, such as oil or water, or some other liquid, contained in a pan which is disposed on the floor of the incubator assembly.

The incubator assembly preferably also includes a timer which monitors the incubation time during which a filter is used, and which is operable to indicate when the filter being used must be replaced. The preferred procedure for performing this function is by operably connecting some kind of warning device, such as a signal light, with the timer. When the warning device is activated by the timer, the user is alerted that the air filter should be changed. After the filter is changed, the user will reset the timer so that the expiration time of the new filter will be recorded by the timer and the user will be informed that the filter should again be replaced with a new filter.

The following is a listing of several desirable, but non-essential, objects of this invention.

It is an object of this invention to provide an improved embryo growth-supporting incubator apparatus which provides one with improved access to the growth media of individual embryos which are disposed in the incubator apparatus.

It is another object of this invention to provide an apparatus of the character described which enables embryos in growth media plates or tubes to be easily removed from the incubator, examined and returned to the incubator without disturbing other growth media plates or tubes in the incubator.

It is a further object of this invention to provide an incubator apparatus of the character described wherein circulation of the gases in the incubator is promoted by means of the configuration of embryo-supporting shelves in the incubator.

It is another object of this invention to provide an incubator apparatus of the character described wherein the improved gas circulation and the improved access to embryo growth dishes are both provided by the configuration of the embryo-supporting shelves in the incubator.

It is a further object of this invention to provide an incubator apparatus of the character described wherein the atmosphere in the incubator is humidified.

It is another object of this invention to provide an incubator apparatus of the character described wherein the atmosphere in the incubator is recirculated and filtered.

It is an additional object of this invention to provide an incubator apparatus of the character described which includes a timer which activates an indicator when it is time to replace the atmosphere filter unit in the apparatus.

BRIEF DESCRIPTION OF THE DRAWINGS

These and other objects and advantages of the invention will become more readily apparent from the following detailed description of an embodiment of the invention, when taken in conjunction with the accompanying drawing which is a fragmented schematic perspective view of an embryo-culturing incubator which is formed in accordance with this invention.

DETAILED DESCRIPTION OF SPECIFIC EMBODIMENTS OF THE INVENTION

Referring now to the drawing, there is shown a somewhat schematic fragmented perspective view of an embryo culturing incubator assembly, denoted generally by the numeral 2, which is formed in accordance with this invention. The incubator assembly 2 induces an inner compartment 4 which is inside of an outer jacket 6. The jacket 6 may induce heater coils (not shown), and/or may serve as a water jacket. The inner compartment 4 has a plurality of shelves 8 disposed therein, which shelves 8 hold embryo-culturing dishes or tubes 10. The compartment 4 also contains an oil/water pan 12 which contains a supply of a liquid, such as oil or water, for humidifying recirculated gases in the compartment 4. The pan 12 can be formed from stainless steel and can be re-usable, or it can be formed from plastic and be discardable. Air in the inner compartment 4 is constantly filtered and recirculated by means of a filter assembly 14 and an air mover 16, which can be a pump, a blower or a fan which are interconnected by a conduit 18. A return line 20 interconnects the air mover 16 and the humidifying pan 12 so that the recycled gas in the return line 20 will pass through the liquid in the pan 12 before entering the interior of the incubator 2. The entire gas recirculating assembly is preferably disposed in the inner compartment 4. The recirculating assembly serves to continuously remove particulates and gaseous organic compounds from the atmosphere in the inner compartment 4 as described in commonly owned U.S. Pat. No. 6,013,119, granted Jan. 11, 2000. The recirculating assembly also serves to continuously humidify the atmosphere in the incubator inner compartment 4. The incubator assembly 2 also preferably induces an outermost cavity 22. An outer wall 24 of the cavity 22 forms the outermost component of the incubator assembly 2.

The cavity 22 contains a pair of gas inlet lines 26 which are used to provide the desired atmosphere in the inner compartment 4. The lines 26 are connected to separate gas sources such as bottled gases (not shown) of the appropriate gas mixture for the incubator, and lead to a valve assembly 28. A typical gas mixture for use in providing a proper incubator atmosphere can be composed of 95% air and 5% $CO_2$. The atmosphere formulations are typically contained in tanks from which they are drawn off. In certain applications, tri-gas formulations will be utilized for the incubator atmosphere. A single line 30 extends from the valve assembly 28 to a bubbler 32. A subsequent line 34 extends from the bubbler 32 into the interior of the inner compartment 4. In this manner, the gas entering the interior of the incubator 2 from the gas source tanks will pass through the liquid in the bubbler 32 so that any impurities such as benzene, isopropanol, butaine, acetone, or the like which may be in the bottled gas will be removed from the entering gas stream in the bubbler, and the entering gas stream will also be humidified. Separate gas sources are preferred, so that when one is depleted, the other can be activated, and the depleted gas source can be replaced. To this end, the valve assembly 28 serves to switch the connections between the operative gas inlet line 26 to the outlet line 30 when a gas source is sensed to be depleted. The bubbler 32 humidifies the incoming incubator assembly gases. Thus, both incoming and recirculated incubator gases are humidified to the degree required for proper incubation of embryos in the incubator assembly 2.

The cavity 22 is formed by the outer wall 24 and an inner intermediate wall 23. Electrical power boxes 36 and 38 may be mounted on the wall 23. The power box 38 supplies electrical power to humidity, temperature, pump power, and other operating sensors which form a part of the assembly 2. The power box 36 supplies electrical power to a computer controller 40 which controls and monitors all of the essential operating conditions needed for proper operation of the incubator assembly 2. A keypad 42 is used by a technician for setting incubator operating conditions in the controller 40. The keypad 42 also preferably includes a timer which controls activation of a signal light 43 that will be illuminated when it is time to change the filter unit 14. The filter unit also includes a timer reset button 15 which is operative to reset the timer when the filter unit 14 is changed. The incubator assembly 2 includes a door opening 44 for accessing the interior of the compartment 4. The door opening 44 is equipped with a door (not shown) and the incubator assembly 2 includes a top wall 46.

The shelves 8 are provided with a plurality of openings 48 which enhance circulation of the gas mixture in the compartment 4. The shelves 8 are also provided with frontal central recesses 50 which face the door opening 44 of the incubator assembly 2. The recesses 50 provide easy access to the interior of the incubator cavity 4 so that one can easily reach into the cavity 4 via the recesses 50 and remove any one of the culturing dishes 10 from any one of the shelves 8 without having to reach over any of the other dishes 10 on the shelves 8. This advantage minimizes the likelihood of any of the dishes 10 being accidentally knocked off of a shelf 8 by a technician reaching for another one of the dishes 10. The recesses 50 also serve to further enhance circulation of incubation gases in the cavity 4. The shelves 8 may also be provided with reinforcing and structurally strengthening flanges 52. It will be noted that the recesses 50 in the shelves create a front edge on the shelves whose length is greatly increased as compared to a shelf having a straight front edge. This allows a greater number of culture dishes 10 to be positioned in the "front row" on each of the shelves 8. The shape of the recesses 50 are illustrated as curvilinear in the drawing, however it will be appreciated that they could also be rectilinear with adjacent linear or straight sections.

It will be readily appreciated that the central recesses in the incubator shelves provide for ready access to the culturing dishes and also enhance circulation of incubator gases inside of the incubating compartment. The result is that the embryos being grown in the incubator will be exposed to a more homogeneous gaseous environment and will also be more easily removed and examined during their incubation growth period. It will be noted that the central recesses in the shelves are dimensioned so as to allow each one of the culturing dishes to be reached manually without having to reach over any of the other culturing dishes. Due to the presence of the central recesses, each of the shelves holds a single file curved row array of culturing dishes, each one of which dishes is proximal to the recess. The humidifying and filtering of the atmosphere in the incubator and the provision of a filter-life timer improves the success rate of the in vitro fertilization process being performed in the incubator.

Since many changes and variations of the disclosed embodiment of the invention may be made without departing from the inventive concept, it is not intended to limit the invention except as required by the appended claims.

What is claimed is:

1. An incubator apparatus for use in culturing biological specimens contained in culturing dishes, said apparatus comprising:

a) a rectangular specimen-culturing compartment, said culturing compartment including an opening in a wall thereof for accessing specimen-culturing dishes disposed in said culturing compartment; and b) at least one shelf in said culturing compartment, said shelf having back and side edges which abut back and side walls of said compartment, said shelf having a an open front edge which is accessible via said culturing compartment opening, said front edge of said shelf having a central recess which faces said opening so that said front edge indudes back and side portions having a planar upper culturing dish-supporting surface, said portions being essentially parallel to back and side walls of said compartment, said recess being operable to effectively increase the length of said front edge of said shelf to a degree which increases the number of specimen-culturing dishes that can be placed on said shelf dish-supporting surface and immediately adjacent to said front edge of said shelf.

2. The apparatus of claim 1 wherein said shelf is sized so that only one specimen-culturing dish can be positioned adjacent to said front edge of said shelf at all locations on said shelf.

3. The apparatus of claim 1 wherein said central recess in said shelf is sized so as to enable one to manually reach into said culturing compartment to gain access to each culturing dish on said shelf without having to reach over any other culturing dishes on said shelf.

4. The apparatus of claim 1 wherein said culturing compartment is provided with a plurality of substantially identically configured recessed shelves.

5. The apparatus of claim 1 wherein said central recess in said shelf is sized so as to provide a sufficient culturing dish support surface so that only a single file array of culturing dishes can be disposed on said support surface.

\* \* \* \* \*